United States Patent
Tammen et al.

(10) Patent No.: US 8,673,574 B2
(45) Date of Patent: Mar. 18, 2014

(54) DIAGNOSIS AND MONITORING OF RENAL FAILURE USING PEPTIDE BIOMARKERS

(75) Inventors: Harald Tammen, Hanover (DE); Leif Honda, Rye, NH (US); Michael Jurgens, Hanover (DE); Andrew Peck, Waltham, MA (US)

(73) Assignee: PxBioSciences LLC, Waltham, MA (US)

( * ) Notice: Subject to any disclaimer, the term of this patent is extended or adjusted under 35 U.S.C. 154(b) by 790 days.

(21) Appl. No.: 12/544,605

(22) Filed: Aug. 20, 2009

(65) Prior Publication Data

US 2010/0190164 A1 Jul. 29, 2010

Related U.S. Application Data

(60) Provisional application No. 61/090,853, filed on Aug. 21, 2008.

(51) Int. Cl.
*G01N 33/53* (2006.01)

(52) U.S. Cl.
USPC .......................................................... 435/7.1

(58) Field of Classification Search
None
See application file for complete search history.

(56) References Cited

U.S. PATENT DOCUMENTS

| | | | | |
|---|---|---|---|---|
| 6,900,016 | B1 * | 5/2005 | Venter et al. | 435/6.14 |
| 8,039,227 | B2 * | 10/2011 | Klein et al. | 435/7.92 |
| 2003/0119058 | A1 | 6/2003 | Qvist et al. | |
| 2006/0067881 | A1 | 3/2006 | Groman et al. | |
| 2006/0258560 | A1 | 11/2006 | Yang et al. | |
| 2008/0090304 | A1 | 4/2008 | Barasch et al. | |
| 2008/0188449 | A1 | 8/2008 | Crews et al. | |

OTHER PUBLICATIONS

Nephrol. Dial. Transplant, vol. 17(Suppl. 7): 7-15 (2002).
Herget-Rosenthal, S. et al., "Early detection of acute renal failure by serum cystatin C," Kidney Int'l., vol. 66: 1115-1122 (2004).
Levey, A.S. et al., "Definition and classification of chronic kidney disease: A position statement from Kidney Disease: Improving Global Outcomes (KDIGO)," Kidney Int'l., vol. 67: 2089-2100 (2005).
Lameire, N. et al., "Acute Renal Failure," The Lancet, vol. 365: 417-430 (2005).
Harlow & Lane, Antibodies: A Laboratory Manual, pp. 59-81; 88-173; and 148-173 (1988).
Goding, Monoclonal Antibodies: Principles and Practice, pp. 59-104; and 281-291 (2d ed. 1986).
Kohler & Milstein, "Continuous cultures of fused cells secreting antibody of predefined specificity," Nature vol. 256: 495-497 (1975).
Huse et al., "Generation of a large combinatorial library of the immunoglobulin repertoire in phage lambda," Science, vol. 246: 1275-1281 (1989).
Ward et al., "Binding activities of a repertoire of single immunoglobulin variable domains secreted from *Escherichia coli*," Nature, vol. 341: 544-546 (1989).
Ozmen, S. et al., "Clinical Study: Parathyroid Hormone as a Marker for the Differential Diagnosis of Acute and Chronic Renal Failure," Ren. Fail., vol. 29: 509-512 (2007).
Ienaga, K. et al., "Clinical Study: Urinary Excretion of Cratol, an in Vivo Biomarker of Hydroxyl Radical, in Patients with Chronic Renal Failure," Ren. Fail., vol. 29: 279-283 (2007).
Yamada, H. et al., "1,5-Anydroglucitol as a Marker for the Different Diagnosis of Acute and Chronic Renal Failure," Nephron, vol. 73: 707-709 (1996).
International Search Report for International Application No. PCT/US09/54413 mailed Mar. 3, 2010. 1 page.

* cited by examiner

*Primary Examiner* — Yunsoo Kim
(74) *Attorney, Agent, or Firm* — Wilmer Cutler Pickering Hale and Dorr LLP

(57) ABSTRACT

Methods for the determination of renal failure, especially chronic renal failure and acute kidney injury, by measurement of peptide or protein biomarkers are described. The methods are useful to determine stages of renal failure, especially the early stages such as stage 1, 2, and 3 of chronic renal failure and stages R and I of acute kidney injury. Furthermore there are described peptides and test kits used in the invention. The described methods are intended to replace or complement the measurement of creatinine and/or cystatin C and/or NGAL for diagnosis of renal failure.

30 Claims, 1 Drawing Sheet

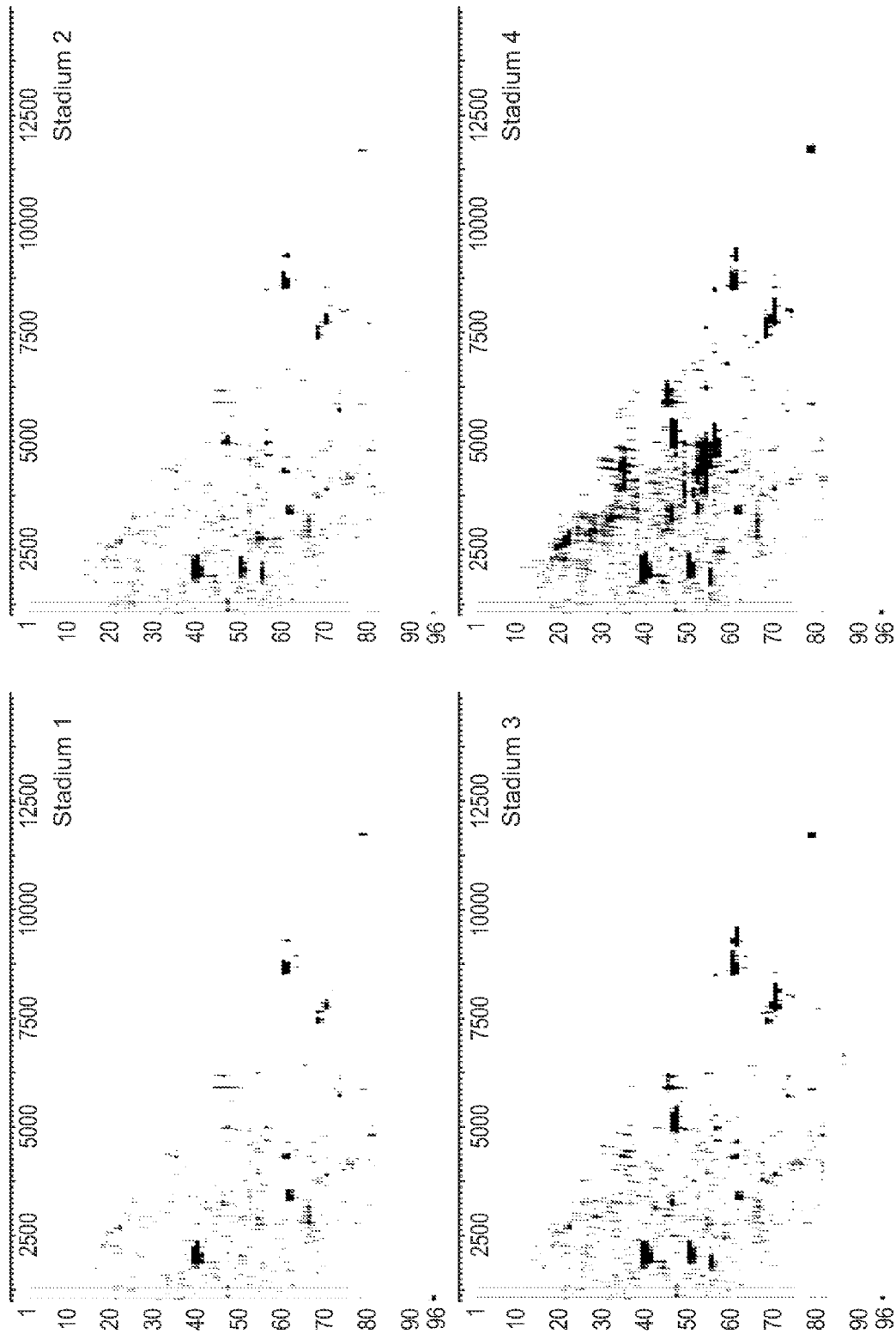

SEQUENCE LISTING

```
<160> NUMBER OF SEQ ID NOS: 2

<210> SEQ ID NO 1
<211> LENGTH: 36
<212> TYPE: PRT
<213> ORGANISM: Homo sapiens

<400> SEQUENCE: 1

Ala Gly Pro Pro Gly Pro Pro Gly Pro Pro Gly Thr Ser Gly His Pro
1               5                   10                  15

Gly Ser Pro Gly Ser Pro Gly Tyr Gln Gly Pro Pro Gly Glu Pro Gly
            20                  25                  30

Gln Ala Gly Pro
        35

<210> SEQ ID NO 2
<211> LENGTH: 17
<212> TYPE: PRT
<213> ORGANISM: Homo sapiens

<400> SEQUENCE: 2

Glu Leu Glu Pro Pro Glu Gln Gln Glu Pro Gly Glu Arg Gln Glu Pro
1               5                   10                  15

Ser
```

DIAGNOSIS AND MONITORING OF RENAL FAILURE USING PEPTIDE BIOMARKERS

RELATED APPLICATIONS

This application claims the benefit of priority to U.S. Provisional Application No. 61/090,853, filed Aug. 21, 2008, the specification of which is incorporated by reference in its entirety.

FIELD OF THE INVENTION

The application relates to biomarkers and methods for the diagnosis of renal failure. The invention targets to diagnose all stages of chronic renal failure, including early stages which are difficult to determine with commonly used diagnostic methods known in the art. The biomarkers and methods of the invention are also used for the diagnosis of acute renal failure or acute kidney injury. The advantage of the invention is that the kidney function can be described accurately and therefore renal failure can be detected at early stages and tracked through all stages of progression.

BACKGROUND OF THE INVENTION

Renal failure is distinguished between acute renal failure or acute kidney injury and chronic renal failure. The basic difference between acute and chronic renal failure is the progression of the disease, which is fast for acute renal failure (usually within days or weeks) and slow for chronic renal failure (usually in the range of years). Both acute renal failure and chronic renal failure can result in a complete loss of renal function, causing the subject to depend on renal replacement therapy, such as hemodialysis or kidney transplantation. The incidence of renal failure has doubled since 1990, most likely caused by the increase of the incidence of diabetes and hypertension, the two major causes for kidney failure.

Chronic renal failure is an irreversible destruction of renal function and usually is associated with the decreased size of the kidneys. It does not cause pain, which is an important reason that it is often not diagnosed until late stages, reducing the success rate of therapy. Treatment usually is started when the kidneys are already largely and irreversibly destroyed. In contrast, acute renal failure can be reversible, depending on its cause and on the success of the therapy. The success of the therapy depends, to a large extent, on the early diagnosis.

Renal failure can be determined by calculating the glomerular filtration rate (GFR). The GFR describes the total volume of primary urine which is filtered by both kidneys within a distinct time interval. The GFR is normally >90 ml/min/body surface. It can be calculated by measuring either exogenic markers or endogenic markers.

Specifically, the GFR can be determined by injecting known amounts of exogenic diagnostic substances such as Inulin, radioactive substances (such as Chromium (Cr51-EDTA), Technetium (99mTC-DTPA), and Cobalt (Co57-vitamin B12)), or radiopaque material (such as Iohexol and Iothalamate), and subsequently measuring the excretion of these substances.

However, these tests are time-consuming, inconvenient, and expensive as they require collecting and measuring the blood and/or the urine excreted repeatedly over a specified time period. Other disadvantages are the use of potentially harmful materials, such as radioactive or radiopaque materials, and the use of expensive and difficult to measure substances, such as Inulin. Thus, calculating the GFR using exogenic substances is usually only used in scientific studies and not clinical practice.

Renal failure can also be determined using endogenic biomarkers, among which serum creatinine clearance is the most commonly used in clinical practice. Creatinine originates from muscle tissue and is increasingly secreted by renal tubules with decreasing renal function. Creatinine clearance can be used to diagnose chronic, as well as acute, renal failure.

Serum creatinine levels depend on age, sex, diet, muscle mass, ethnic background, physical activity, and disease. It is also secreted by the tubuli of the kidneys independent of kidney disease (Nephrol Dial Transplant, 2002, 17 (Suppl. 7):7-15) or can be secreted via the gut. All these factors impair the reliability of creatinine clearance for diagnosis of renal failure.

Various correction formulas are known to improve the accuracy of creatinine-based GFR determinations, by including additional metadata such as race, weight, body height, and body surface. However, these formulas may not work correctly under certain circumstances. For example, if the subjects are bodybuilders, vegetarians, obese, or suffer from diabetes, hypertension, or chronic liver disease. In addition, these formulas are not useful in determining the GFR of healthy subjects or of subjects suffering from only mild or moderate renal failure. Finally, the GFR may decline as much as 50% before serum creatinine starts to increase above reference levels. These limitations demonstrate that correction formulas often are not suitable for all stages of renal failure (from mild GFR reduction to renal failure).

Another endogenic biomarker for renal failure diagnosis is Cystatin C, a 120 amino acid, 20 kDa cysteine-protease inhibitor present in most body fluids. It is excreted by the kidneys. In contrast to creatinine, the expression of Cystatin C is relatively constant, independent of, e.g., muscle mass, body weight and age. Consequently Cystatin C is used as a biomarker of chronic renal failure. Some newer studies also indicate that it might also be useful as a diagnostic marker for acute renal failure (Kidney Int'l., 2004, 66:1115-1122). However, this has to be further investigated.

Cystatin C can be determined directly from blood samples. Therefore, there is no need for the time-consuming, inconvenient and error prone urine collection. Nevertheless, there are still limitations for timely and sensitive diagnosis of renal failure using Cystatin C. In addition, the suitability of Cystatin C for diagnosis of acute renal failure has not yet been validated.

NGAL is another promising endogeneous marker that appears to detect early stages of acute renal injury. NGAL has been shown to correlate with acute kidney injury in a variety of disease modalities and is detectable at an early stage of disease. The validity of NGAL for diagnosis of acute renal failure has yet to be fully determined.

Early detection and intervention is critical to effective treatment of effective treatment. However, the existing diagnosis methods have many disadvantages and limitations as described. Therefore, a need exists for novel methods for early diagnosis of renal failure.

BRIEF SUMMARY OF THE INVENTION

The present invention provides biomarkers, methods, and test kits for diagnosis of renal failure. In one aspect, the renal failure is chronic renal failure. In another aspect, the renal failure is acute renal failure.

The present invention provides a peptide biomarker having the sequence of SEQ ID NO:1 or 2. The present invention also provides a nucleic acid encoding a peptide biomarker having the sequence shown in SEQ ID NO:1 or 2. The present invention further provides an antibody that specifically binds to a peptide biomarker having the sequence shown in SEQ ID NO:1 or 2. Also disclosed is a nucleic acid molecule, or a recombinant nucleic acid molecule consisting of a polynucleotide encoding the biomarker.

The present invention provides a method of identifying a subject having or at risk of developing a renal disorder. The method comprises obtaining a test biological sample from the subject, and determining the quantity of a peptide biomarker in the test biological sample. In one embodiment, the biomarker is selected from the group consisting of SEQ ID NOs: 1 and 2.

In one aspect, the method further comprises the steps of obtaining a control biological sample from a control subject not having and not at risk of developing a renal disorder, determining the quantity of the peptide biomarker in the control sample, and comparing the quantity of the biomarker in the test sample and in the control sample. A variance of the quantity of the biomarker in the test sample relative to the control sample indicates that the subject has or is at risk of developing the renal disorder.

In another aspect, the method comprises comparing the quantity of the biomarker with a predetermined reference value. A variance of the quantity of the biomarker in the test sample relative to the reference value indicates that the subject has or is at risk of developing a renal disorder.

The present invention also provides a method of monitoring the progression or regression of a renal disorder in a subject in need thereof, the method comprises obtaining a test biological sample from a subject and determining the quantity of a peptide biomarker in the test biological sample over a period of time. The quantity of the biomarker correlates to a stage of the renal disorder. A difference of the quantities of the biomarker over a period of time is indicative of the progression or regression of the renal disorder. In one embodiment, the biomarker is selected from the group consisting of SEQ ID NOs: 1 and 2.

The present invention further provides a method of monitoring the efficacy of a renal disorder therapy in a subject in need thereof, the method comprises obtaining a test biological sample from a subject, and determining the quantity of the peptide biomarker in the test biological sample prior to and subsequent to the therapy. The quantity of the peptide biomarker obtained prior to therapy is compared to the quantity of the peptide biomarker obtained subsequent to therapy. The difference is indicative of the efficacy of the renal disorder therapy. In one embodiment, the renal disorder therapy is the administration of medication. In another embodiment, the renal disorder therapy is hemodialysis. In yet another embodiment, the renal disorder therapy is kidney transplantation. The biomarker is selected from the group consisting of SEQ ID NOs: 1 and 2, and the quantity of the biomarker correlates to a stage of the renal disorder.

The present invention further provides a method of determining the renal-toxic side effects of substances (such as medications, chemicals, and microbial or other toxins), living organisms (such as plant, animal, and microbes), and environmental influences (such as food ingestion, alcohol ingestion, consumption of tobacco products, stress, and physical activity), on a human or an animal. A first test biological sample is obtained from the subject prior to the event, and a second test biological sample from the subject is obtained after the event. The quantities of a peptide biomarker in the first test sample and the second test sample are determined. The quantity of the biomarker correlates to a stage of the renal disorder. The difference between the quantities is indicative of the effect of the event on renal function.

In certain embodiments of all the aspects, the subject is selected from the group consisting of a human, a primate, a mouse, a dog, a pig, and a rat. The methods of the present invention can be used to determine the stages of renal failure. In one aspect, the methods of the present invention can be used to determine stages 1, 2, 3, 4, and 5 of chronic renal failure. In another aspect, the methods of the present invention can be used to determine stages Normal, R, I, F, L, and E of acute renal failure.

In certain embodiments of all the aspects, the quantity of the biomarker is determined by calculating glomerular filtration rate. The biological sample is selected from the group consisting of blood, plasma, serum, hemofiltrate, urine, kidney tissue, in vitro cultured kidney cell lines, in vitro cultured primary kidney cells, in vitro cultured kidney tissue, in vitro cultured kidney organ, and supernatants from in vitro cell culture, tissue culture, and organ culture.

Certain embodiments of the aspects may further include a method of injecting the subject with an exogenic substance and calculating glomerular filtration rate by measuring the clearance of the exogenic substance. The exogenic substance can be Inulin, a radioactive substance (e.g., Cr51-EDTA, 99mTC-DTPA, and Co57-vitamin B12), or a radiopaque material (e.g., Diatrizoates, Iodipamide, Iohexol, Iopamidol, Ioversol, Iothalamate, Ioxaglate, and Metrizamide). The glomerular filtration rate can be calculated by measuring the clearance of an endogenic substance. The endogenic substance can be selected from the group consisting of serum creatinine, Cystatin C, NGAL, urea, interleukin 18, intestinal form of alkaline phosphatease, N-acetyl-beta-gulcosaminidase, alanine-aminopeptidase, kidney injury molecule 1, parathyroid hormone, creatol, creatine kinase, methylguanidine, and 1,5-anhydroglucitol (1,5-AG).

In certain embodiments, the subject has a condition selected from the group consisting of injury to a kidney, type 2 diabetes, hypertension, cardiovascular disease, sepsis, hemorrhage, massive blood loss, congestive heart failure, decompensated liver cirrhosis, damaged kidney blood vessels, obstructions of urine collection systems or extra-renal drainage, vasculitis, malignant hypertension, acute glomerulonephritis, acute interstitial nephritis, and acute tubular necrosis. Further, in certain embodiments, the event is selected from the group consisting of exposure to a substance, exposure to a living organism, food ingestion, alcohol ingestion, consumption of tobacco products, exposure to stress, and physical activity. The substance can be selected from the group consisting of a medication, a chemical, and a toxin. The living organism can be selected from the group consisting of a plant, an animal, a microbe, and a virus.

In certain embodiments, the size of the kidneys is determined, urine output is measured, urine sediments are analyzed, and excretion of sodium or urea is analyzed. Kidney size can be determined using an imaging technique, e.g., ultrasound.

In yet another aspect, the step of determining the quantity of the biomarker is accomplished by an immunological method (e.g., an ELISA assay, an RIA assay, an ELI-Spot assay, a flow cytometry assay, an immunohistochemistry assay, a Western blot analysis, and a protein chip assay), a molecular biologic method (e.g., PCR analysis, a RT-PCR analysis, a TaqMan PCR analysis, a nucleic acid chip assay, in situ hybridization, a nucleic acid dot blot analysis, a nucleic acid slot blot analysis, a Southern blot analysis or a Northern blot analysis), or a physical method (e.g., mass spectrometric method, a FRET assay, a chromatographic assay, or a dye-detection assay). The mass spectrometric method can be a MALDI, ESI, ionspray, thermospray, MCI, FAB, SELDI, ICAT, iTRAQ, or affinity mass spectrometric method. In certain aspects, the step of determining the quantity of the biomarker can be accomplished by nuclear magnetic resonance (NMR), fluorometry, colorimetry, radiometry, luminometry, liquid chromatography, capillary chromatography, thin-layer chromatography, plasmon-resonance (e.g. BIACORE), or one- or two-dimensional gel electrophoresis.

The biological sample can be fractionated prior to the detection step. Fractionating can be done through a method selected from the group consisting of a chromatography method, a filtration method, a capillary electrophoresis method, a gel electrophoresis method, a liquid extraction method, a precipitation method, and an immunoprecipitation method. Further, the chromatography method can be reverse phase chromatography.

The methods of the present invention can be combined with known diagnostic methods using markers or procedures such as creatinine clearance, Cystatin C, or other markers for renal failure, or with measuring urine output, measuring the size of the kidneys, analysis of urine sediments and excretion of sodium or urea to further improve the overall sensitivity and/or specificity of the diagnosis of renal failure.

Another aspect of the invention is the pre-analysis of a diagnostic sample intended for other non-renal failure diagnostic procedures. The pre-analysis determines whether renal failure is present, as renal failure might impair other markers for non-renal failure diseases or conditions, which are intended to be measured using the same sample.

The present invention further provides a test kit for diagnosing, monitoring the progression or regression, or monitoring the treatment of a renal disorder. In one aspect, the kit comprises a peptide biomarker, a nucleic acid molecule consisting of a polynucleotide encoding a peptide biomarker, or a recombinant nucleic acid molecule consisting of a polynucleotide encoding a peptide biomarker having the sequence of SEQ ID NO:1 or 2. In yet another aspect, the kit comprises an antibody specifically binds to a peptide biomarker having the sequence shown in SEQ ID NO:1 or 2. In one embodiment, the kit of the present invention may optionally comprise instructions for diagnosing, monitoring the progression or regression, or monitoring the treatment of the renal disorder. In certain aspects, instructions to detect the biomarker in the biological sample are included in the kit.

BRIEF DESCRIPTION OF THE FIGURES

FIG. 1 depicts Peptide Displays of different stages of chronic renal failure.

DETAILED DESCRIPTION OF THE INVENTION

The present invention provides biomarkers, methods, and test kits for diagnosis of renal failure. In one aspect, the renal failure is chronic renal failure. In another aspect, the renal failure is acute renal failure. "Chronic renal failure" is used interchangeably with chronic renal disease, and "acute renal failure" is used interchangeably for acute renal disease, and/or acute kidney injury. Renal failure is regarded as chronic if it persists for at least 3 months.

The stages (alternatively termed states, classes or grades) of chronic renal failure are defined by the GFR as stated in Table 1 (Kidney Int'l., 2005, 67:2089-2100).

TABLE 1

Stages of chronic renal failure

| Stage | GFR (mL/min) | Description |
|---|---|---|
| 1 | ≥90 | Normal or elevated GFR |
| 2 | 60-89 | Mild GFR reduction |
| 3 | 30-59 | Moderate GFR reduction |
| 4 | 15-29 | Severe GFR reduction |
| 5 | <15 | Renal failure |

Acute renal failure is classified into 5 distinct stages using the "RIFLE" (Risk, Injury, Failure, Loss, End-stage renal disease) staging system as shown in Table 2 (The Lancet, 2005, 365:417-430). The first 3 stages are distinguished based on both increased serum creatinine levels and reduced urine output.

TABLE 2

Stages of acute renal failure

| Stage | GFR (based on serum creatinine) criteria | Urine output criteria |
|---|---|---|
| Risk | Serum creatinine increased 1.5 times | <0.5 mL/kg/h for 6 h |
| Injury | Serum creatinine increased 2.0 times | <0.5 mL/kg/h for 12 h |
| Failure | Serum creatinine increased 3.0 times, or creatinine >355 mM/L when there was an acute rise of >44 mM/L | <0.3 mL/kg/h for 24 h, or anuria for 12 h |
| Loss | Persistent acute renal failure >4 weeks | — |
| End-stage | End-stage renal disease >3 months | — |

Other staging methods for renal failure resulting in similar or comparable classifications of different stages of renal failure may be used according to the invention.

Determining the presence or absence of renal failure means to determine if renal failure, including chronic renal failure or acute renal failure, is present or is not present in a subject. This includes the determination of any stage of the chronic renal failure, e.g., stages 1-5 of the chronic renal failure shown in Table 1. It also includes the determination of any stage of the acute renal failure, e.g., stages RIFLE of the acute renal failure shown in Table 2. It further includes distinguishing the stages of renal failure, e.g., distinguishing stage 1 from stages 2 and/or 3, or distinguishing stages 1, 2, or 3 from stages 4 and/or 5.

Samples and Subjects

Any sample containing peptides and/or proteins from a subject to be tested for the presence or absence of renal failure can be used according to the invention. The sample can be whole blood, plasma, serum, hemofiltrate, urine, kidney or other tissue, or a fraction thereof or a combination of the samples. The sample may also originate from in vitro cultured cell lines, or primary cells, or from in vitro cultured tissue or organs, especially kidneys, or from cell culture, tissue culture, or organ culture supernatants.

The sample may be pooled samples collected during a certain period of time or of more than one subject. It can be used directly or after storage for various time periods at various storage conditions. The sample may or may not be pre-processed, e.g., fractionated by chromatography, filtration, capillary electrophoresis, precipitation, liquid or other extraction methods, and immunoprecipitation.

The subject from which the sample originates can be a human or an animal used for experimental testing, preferably a mammal, such as a primate, a dog, a pig, or a rodent, including, e.g., a mouse or a rat.

Specifically, subjects having vascular diseases, including bilateral renal artery stenosis, ischemic nephropathy, hemolytic-uremic syndrome, and vasculitis, are more likely to develop chronic renal failure. Other causes of chronic renal failure include, but not limited to, focal segmental glomerulosclerosis, IgA nephritis, diabetic nephropathy, lupus nephritis, polycystic kidney disease, drug and toxin-induced chronic tubulointerstitial nephritis, kidney stones, and prostate diseases.

Causes of acute renal failure are divided into 3 main groups: pre-renal, post-renal and intra-renal. Pre-renal causes include lack of sufficient blood supply of the kidneys, which in turn may be caused by hemorrhage, massive blood loss, congestive heart failure, decompensated liver cirrhosis (liver cirrhosis with complications such as bleedings, ascites), damaged kidney blood vessels, sepsis, or systemic inflammation due to infection. Post-renal causes include obstructions of urine collection systems or extra-renal drainage, which in turn may be caused by medication interfering with normal bladder emptying, prostate diseases, kidney stones, abdominal malignancy (such as ovarian cancer or colorectal cancer), or obstructed urinary catheter. Intra-renal causes are renal tissue-destroying effects, such as vasculitis, malignant hypertension, acute glomerulonephritis, acute interstitial nephritis and acute tubular necrosis. They can be caused by, e.g., ischaemic events (such as hemoglobinuria, myoglobinuria, and myeloma) or by nephrotoxic substances (such as antibiotics, radio contrast agents, uric acid, and oxalate). Subjects suffering from these diseases and conditions are more likely to develop acute renal failure.

Biomarkers as Diagnostics for Renal Failure

A biomarker is an organic biomolecule present in a sample used to determine the phenotypic status of the subject or predict a physiological outcome (e.g., health or disease state). A biomarker is differentially present between different phenotypic statuses if the mean or median expression level of the biomarker in the different groups is calculated to be statistically significant. A single biomarker, or a combination of particular biomarkers, provides measures of relative risk or probability that a subject belongs to one phenotypic status or another or will develop membership to a specific phenotypic status. Therefore, they are useful as biomarkers for disease (diagnostics), therapeutic effectiveness of a drug (theranostics), drug toxicity, and predicting and identifying the immune response.

Biomarkers according to the invention include proteins, protein fragments, peptides, and nucleic acids.

Peptides and Proteins

In one aspect, the present invention provides a peptide biomarker having the sequence of AGPPGPPGPPPGTSGH-PGSPGSPGYQGPPGEPGQAGP (SEQ ID NO:1). This peptide is a fragment of the full length protein Collagen alpha-1 (III) (P02461). The present invention also provides a peptide biomarker having the sequence of ELEPPEQQEPGERQEPS (SEQ ID NO:2). This peptide is a fragment of the full length protein Integrin alpha-7 (Q13683).

The term "peptide" refers to compounds consisting of two or more amino acids joined covalently by peptide bonds having a molecular mass of 0.5 to 20 kDa. The term "protein" refers to a polypeptide bigger than a peptide.

A full length protein refers to the complete sequence of a protein with the signal sequence. For example, full length human cystatin C (NP_000090) has 146 amino acid residues. Fragments of full length proteins are considered peptides, including signal sequences and other sequences created during proteolytic or other processing, fragments such as pro-peptide sequences, as long as the fragments have at least 7 amino acid residues and can be identified as originating form the parent protein sequence by use of standard sequence alignment algorithms as known in the art, such as the BLAST or FASTA algorithms. For example, amino acids 1-26 of the full length human cystatin C (NP_000090) is a signal peptide.

The terms "peptide" and "protein" according to the invention include compounds containing only amino acids, as well as compounds also containing non-amino acid constituents such as carbohydrates and lipid structures and include compounds containing only peptide bonds as well as compounds containing other bonds, e.g. ester, thioether or disulfide.

The peptides of the present invention can be fragments of proteins present in nature. Peptides and proteins may contain postranslational modifications such as phosphate groups, carbohydrate groups or lipid moieties. Also included are peptides and proteins that comprise amino acids different from the standard set of 20 amino acids coded by the genetic code.

Modifications of peptides or proteins according to the invention may comprise modifications due to postranslational modifications, chemical modifications, enzymatic modifications and modifications due to other mechanisms. Examples of possible modifications include but are not limited to: glycosylation, phosphorylation, sulphatation, pyroglutamate modification, cystein-disulfide bridges, methylation, acetylation, acylation, farnesylation, formylation, geranylgeranylation, biotinylation, stearoylation, palmitylation, lipolyation, C-mannosylation, miristoyliation, amidation, deamidation, methylation, demethylation, carboxylation, hydroxylation, iodination, oxidation, pegylation, prenylation, ADP-ribosylation, addition of lipids, of phosphatidylinositol, of glycosylphosphatidylinositol (GPI)-anchor, of pyridoxal phosphate, modification of cystein residues resulting in carboxyamidomethylcysteine, resulting in carboxymethylcysteine, or resulting in pyridylethylcysteine, modification of lysine residues resulting in liponic acid, modification of glutamic acid resulting in pyroglutamic acid.

Modifications of peptides or proteins according to the invention may comprise unusual amino acids, chemically or enzymatically modified amino acids including, but not limited to: alpha amino butyric acid, beta amino butyric acid, beta amino iso-butyric acid, beta alanine, gamma butyric acid, alpha amino adipic acid, 4-amino benzoic acid, amino ethyl cysteine, alpha amino penicillanic acid, allysine, 4-carboxy glutamic acid, cystathionine, carboxy glutamic acid, carboxy amido methyl cysteine, carboxy methyl cysteine, cystein acid, citrulline, dehydroalanine, di-amino butyric acid, dehydro amino-2-butyric acid, ethionine, glycine-proline di-peptide, 4-hydroxyproline, hydroxylysine, hydroxyproline, homoserine, homo cysteine, histamine, iso-valeine, lysinoalanine, lanthionine, norvaline, norleucine, ornithine, 2-pipiridine-carboxylic acid, pyroglutamic acid, pyrrolysine, proline-hydroxy proline di-peptide, sarcosine, 4-selenocysteine, syndesine, and thioproline. Further examples can be found in databases such as "Delta Mass" at http://www.abrf.org/index.cfm/dm.home?AvgMass=all.

Nucleic Acids, Complementary and Degenerated Nucleic Acids and Derivatives

In another aspect, the present invention provides a nucleic acid encoding the peptide biomarker having sequence of SEQ ID NO:1 or 2. The present invention also provides a recombinant nucleic acid containing the nucleic acid sequence encoding the peptide biomarker of SEQ ID NO:1 or 2.

Nucleic acids are deoxyribonucleic acids (DNA), ribonucleic acids (RNA), or combinations thereof, regardless if the nucleic acid molecules are single or double-stranded, linear, circular or branched. It will be understood that when a nucleotide sequence is represented by a DNA sequence (i.e., A, T, G, C), this also includes an RNA sequence (i.e., A, U, G, C).

The nucleic acid molecules are purified nucleic acid molecules, i.e., the preparation contains at least 50%, and preferably higher, of a certain nucleic acid molecule or of a certain mixture of more than one certain nucleic acid molecule. Examples of nucleic acid molecules are genomic DNA, cDNA (complementary DNA), mRNA (messenger RNA), recombinantly produced nucleic acid molecules corresponding to the natural sequences, chemically synthesized nucleic acid molecules corresponding to the natural sequences, or nucleic acid molecules generated by enzymatic methods (such as by use of polymerase chain reaction (PCR)), or nucleic acid molecules purified from natural sources (such as prokaryotic or eukaryotic cells, blood cells, body fluids such as plasma, serum, urine, biopsy material (especially kidney biopsy material), using methods known in the art.

Furthermore, nucleic acid molecules according to the invention can be partial or complete derivatives of nucleic acids, including nucleotides or nucleotide-like molecules not found in nature (such as phosphorothioates, peptide nucleic acids (PNAs), N3', P5'-phosphoramidates, morpholino phosphoroamidates, 2'-O-methoxyethyl nucleic acids, 2'-fluoro-nucleic acids, arabino-nucleic acids, and locked nucleic acids (LNA, ribonucleotides containing a methylene bridge that connects the 2'-oxygen of ribose with the 4'-carbon)).

Antibodies

In another aspect, the present invention provides an antibody that specifically binds to the peptide biomarker having the sequence of SEQ ID NO:1 or 2. Such an antibody may be polyclonal or monoclonal. The antibodies of the present invention are useful in the methods and test kits of the invention. For example, after an antibody is provided, a peptide marker can be detected and/or quantified using any of a number of well recognized immunological binding assays.

One skilled in the art would readily carry out known techniques in order to raise antibodies against the biomarkers of the invention. See, e.g., Coligan, Current Protocols in Immunology (1991); Harlow & Lane, Antibodies: A Laboratory Manual (1988); Goding, Monoclonal Antibodies: Principles and Practice (2d ed. 1986); and Kohler & Milstein, Nature 256:495-497 (1975). Such techniques include, but are not limited to, antibody preparation by selection of antibodies from libraries of recombinant antibodies in phage or similar vectors, as well as preparation of polyclonal and monoclonal antibodies by immunizing rabbits or mice (see, e.g., Huse et al., Science 246: 1275-1281 (1989); Ward et al., Nature 341: 544-546 (1989)).

Determining a Biomarker

Determining a biomarker includes the qualitative and/or quantitative determination and measurement of biomarkers that are present in biological samples. Depending on the sensitivity of the measurement method used, the determination may detect the presence of a substance, i.e., the quantity of the substance is above the detection limit of the method used, or it may be that the substance is not detectable, i.e., its quantity is below the detection limit of the method used.

If a quantitative determination is performed, the quantity of the substance may be determined as a relative or as an absolute value, depending on the method used. If the determination is absolute, it may be expressed as an exact quantity of the biomarker (e.g., in mg/mL, mmol or M). If the determination is relative, it may be relative to a reference measurement, to a reference or normal value, or to a reference sample. The relative quantity may be expressed, e.g., as a percentage of the reference or in arbitrary units.

Generally, all methods suitable to detect and analyze biomarkers in a sample can be used in the methods of the invention. These methods include physical, immunological, and molecular biology methods.

Suitable physical methods include mass spectrometric methods, fluorescence resonance energy transfer (FRET) assays, chromatographic assays (such as liquid chromatography, capillary chromatography, and thin-layer chromatography), and dye-detection assays. Mass spectrometric methods include, but are not limited to, matrix-assisted laser desorption ionisation (MALDI), continuous or pulsed electrospray ionization (ESI), and related methods such as ionspray or thermospray or massive cluster impact (MCI). The ion sources can be matched with detection formats including linear or non-linear reflection time-of-flight (TOF), single or multiple quadrupole, single or multiple magnetic sector, fourier transform ion cyclotron resonance (FTICR), ion trap, and combinations thereof, e.g. ion-trap/time-of-flight. For ionization, numerous matrix/wavelength combinations (MALDI) or solvent combinations (ESI) can be used. Other suitable mass spectrometric methods are, e.g., fast atom bombardment (FAB) mass spectrometry, Surface Enhanced Laser Desorption/Ionization (SELDI) mass spectrometry, isotope coded affinity tag (ICAT) mass spectrometry, iTRAQ mass spectrometry, and affinity mass spectrometric methods.

Suitable immunologic methods include, but are not limited to, enzyme linked immuno assays (ELISA), sandwich, direct, indirect, or competitive ELISA assays, enzyme-linked immunospot assays (ELISPOT), radio immuno assays (RIA), flow cytometry assays (FACS=fluorescence activated cell sorting), immunohistochemistry, Western blot, protein-chip assays using for example antibodies, antibody fragments, receptors, ligands, or other agents binding the substances, such as the peptides of the present invention. Binding agents can be used to analyze and determine the presence or absence of biomarkers in a sample. The biological sample is contacted with one or more agents that bind to the biomarker to determine the level of expression of the biomarker in the sample. One or more of the agents may be operably linked to a detectable label.

Molecular biology methods that can be used according to the invention include, but are not limited to, Northern or Southern blot hybridization, nucleic acid dot- or slot-blot hybridization, in situ hybridization, nucleic acid chip assays, PCR, reverse transcriptase PCR (RT-PCR), or real time PCR (taq-man PCR).

Other methods to detect biomarkers include, e.g., nuclear magnetic resonance (NMR), fluorometry, colorimetry, radiometry, luminometry, or other spectrometric methods, plasmon-resonance (e.g. BIACORE), and one- or two-dimensional gel electrophoresis.

Furthermore, different methods may be combined to determine a biomarker. For example, the combination of liquid chromatography and mass spectrometry (LC-MS) or the combination of capillary zone electrophoresis and mass spectrometry (CE-MS), or the combination of extraction of certain classes of substances such as peptides, from a sample prior to LC-MS or prior to CE-MS or prior to other methods.

Combination of Methods

The methods of the present invention can be combined with other diagnostic methods for renal failure to improve specificity and selectivity. For example, other diagnostic methods include measurements of exogenic markers, e.g., Inulin, radioactive materials (such as Cr51-EDTA, 99mTC-DTPA, and Co57-vitamin B12), and radiopaque materials (such as Diatrizoates, Iodipamide, Iohexol, Iopamidol, Ioversol, Iothalamate, Ioxaglate, and Metrizamide).

Other diagnostic methods also include measurements of endogenic markers, such as serum creatinine and Cystatin C. Additional biomarkers for renal failure have been described in the literature. For example, biomarkers for acute renal failure include NGAL, urinary interleukin 18, tubular enzymes (such as the intestinal form of alkaline phosphatase, N-acetyl-beta-gulcosaminidase and alanine-aminopeptidase), and kindney injury molecule 1. Some biomarkers, such as parathyroid hormone (parathormone), a peptide hormone, may be used to distinguish acute from chronic renal failure (Ren. Fail., 2007, 29:509-512). In addition, known modified forms of biomarkers for renal failure, such as creatinine modified by hydroxyl radical addition resulting in Creatol (Ren. Fail., 2007, 29:279-283), or enzymes modifying creatine, such as creatine kinase may also be suitable for diagnosis of renal failure. Examples of non-peptide markers for renal failure include methylguanidine (used in combination with creatol), and 1,5-anhydroglucitol (1,5-AG) (used in combination with serum creatinine) (Nephron, 1996, 73:707-709).

Further diagnostic methods include imaging techniques to determine the size of the kidneys (such as ultrasound), measurement of urine volume, analysis of urine sediments, and analysis of urinary chemistry (such as excretion of sodium or urea).

It is possible to combine one or more than one of these diagnostic methods with the method of the invention. In addition, the diagnostic procedures can be done simultaneously or successively to confirm the diagnosis or to increase the sensitivity and/or specificity of the diagnosis.

Use of the Methods and Biomarkers of the Invention

The methods and biomarkers of the invention can be used, among others, for diagnosis of renal failure, including chronic and acute renal failure. The methods and biomarkers of the invention can be used for determining the stages of renal failure, especially early stages of renal failure which are difficult or not at all possible to diagnose using methods known in the art.

The present invention provides a method of identifying a subject having or at risk of developing a renal disorder, the method comprises obtaining a test biological sample from the subject and determining the quantity of a peptide biomarker in the test sample. In one embodiment, the biomarker is selected from the group consisting of SEQ ID NOs: 1 and 2.

In one aspect, the method further comprises the steps of obtaining a control biological sample from a control subject not having and not at risk of developing a renal disorder, and comparing the quantity of the biomarker in the test sample and in the control sample. A variance of the quantity of the biomarker in the test sample relative to the control sample indicates that the subject has or is at risk of developing the renal disorder.

In another aspect, the method further comprises comparing the quantity of the biomarker with a predetermined reference value. A variance of the quantity of the biomarker in the test sample relative to the reference value indicates that the subject has or is at risk of developing a renal disorder.

The methods and biomarkers of the invention can also be used to determine the stages of renal failure. In one aspect, the methods and biomarkers of the invention can be used to distinguish chronic renal failure stages 1, 2, 3, 4 and 5 from each other. In another aspect, the methods and biomarkers of the invention can be used to distinguish acute renal failure stages R, I, F, L and E from Normal and from each other.

Peptide Displays from different stages of chronic renal failure are shown in FIG. 1. To generate Peptide Displays, samples are prepared and separated by means of RP-HPLC (reversed phase high pressure liquid chromatography) and peptides eluting from the HPLC column are collected into 96 fractions. Each fraction is subjected to MALDI-TOF-MS (matrix-assisted laser desorption/ionization time-of-flight mass spectrometry) and the mass spectra of all 96 fractions are combined, resulting in an in silico two-dimensional display of peptide masses, where the x-axis displays the mass-to-charge ratio, the y-axis is determined by the retention time on the RP-HPLC or the fraction number and signal intensity is depicted by color saturation. FIG. 1 demonstrates the accumulation of peptides in blood plasma of subjects.

The present invention also provides a method of monitoring the progression or regression of a renal disorder in a subject in need thereof, the method comprises obtaining a test biological sample from the subject; determining the quantity of a peptide biomarker in the test sample; repeating the steps over a period of time; and comparing the quantity of the biomarker over the period of time. In one embodiment, the biomarker is selected from the group consisting of SEQ ID NOs: 1 and 2.

The present invention further provides a method of monitoring the efficacy of a renal disorder therapy in a subject in need thereof, the method comprises determining the quantity of a peptide biomarker in a test biological sample obtained from the subject prior to and subsequent to the therapy. In one embodiment, the renal disorder therapy is the administration of medication. In another embodiment, the renal disorder therapy is hemodialysis. In yet another embodiment, the renal disorder therapy is kidney transplantation.

The present invention further provides a method of determining the renal-toxic side effects of substances (such as medications, chemicals, and microbial or other toxins), living organisms (such as plant, animal, and microbes), and environmental influences (such as food ingestion, alcohol ingestion, consumption of tobacco products, stress, and physical activity), on a human or an animal.

The methods and biomarkers of the invention can also be used to pre-test a sample to determine if the subject from which the sample originates suffers from kidney failure and for this reason shows an altered excretion profile of other biomarkers intended to be measured for diagnostic purposes. After the methods and biomarkers of the invention have confirmed that the subject from which the sample originates, does not suffer from kidney failure, additional diagnostic biomarkers can be determined, without being in doubt that a possibly underlying kidney failure impairs measurement of the additional diagnostic biomarker. Alternatively the pre-test for kidney failure and the test for the additional biomarker can be done simultaneously, or the results of the pre-test for kidney failure can be converted into a correction factor used to correct the result of the renal-failure-impaired measurement of the additional biomarker, based on the extent to renal failure, or based on correction factors determined for individual biomarkers by empirical testing.

Test Kits

The present invention further provides a test kit for diagnosing, monitoring the progression or regression, or monitoring the treatment of a renal disorder. In one embodiment, the kit comprises a peptide biomarker having the sequence of SEQ ID NO:1 or 2. In another embodiment, the kit comprises a nucleic acid encoding a peptide biomarker having the sequence shown in SEQ ID NO:1 or 2. In yet another embodiment, the kit comprises an antibody that specifically binds to a peptide biomarker having the sequence shown in SEQ ID NO:1 or 2.

The test kit may optionally comprise substances for use as standard and/or controls. The test kit may further optionally comprise known markers for renal failure, such as creatinine or Cystatin C, to further increase overall sensitivity and/or specificity of the test.

In one aspect, the present invention provides test kits for determining the absolute concentration or the relative concentration, or determining the presence or absence of the biomarkers of the present invention, thereby enabling the measurement of renal function and/or diagnosis of renal failure. The test kit can be used to diagnose the absence or presence of renal failure/renal disease. The test kit can also be used to predict the occurrence or to predict the stage of renal failure. The test kit can further be used to predict and/or monitor the success of a therapy for renal failure such as therapy by medications, therapy by dialysis, or therapy by kidney transplantation. Furthermore, the test kits of the present invention can be used for the pre-analysis of a diagnostic sample intended for other non-renal failure diagnostic procedures. The test kits for pre-analysis determines whether renal failure is present, as renal failure might impair other markers for non-renal failure diseases or conditions, which are intended to be measured using the same sample.

The test kit can be used to diagnose and/or predict chronic renal failure at a stage earlier than other diagnostics tests currently available (e.g. at Stage 2), such as creatinine clearance, Cystatin C. The test kit can also be used to early diagnose and/or predict acute renal failure, such as at R-stage or I-stage.

The test kit can be used to analyze samples from a subject such as those samples described previously. The test can be done with pooled samples collected during a certain period of time, e.g., after kidney transplantation, during hemodialysis, or during diseases often associated with renal failure such as sepsis. The test can be done with pooled samples of one or of more than one subject. The sample can be used directly, or after storage of the sample for various time periods at various storage conditions, or the sample can be a pre-processed, for example, the sample can be fractionated by chromatography, filtration, capillary electrophoresis, precipitation, liquid or other extraction methods, and immunoprecipitation. The whole sample or subject or two or more combined fractions of a pre-processed sample, originating from one or more than one samples can be analyzed.

The test can be done once or several times over a period of time to analyze the time course of qualitative or quantitative changes of a biomarker of the invention, e.g., the peptides of Seq ID NOs:1 and 2, the encoding nucleic acids, and fragments or modifications of the peptides and nucleic acids.

Furthermore, the test kit may comprise binding agents for the antibodies binding specifically to the biomarkers of the invention, or antibody fragments binding specifically to their antigen. The binding agents can be present in the test kit in immobilized form, for example immobilized to membranes, to microtiter plates, to mass spectrometric targets, to SELDI chips, to protein chips, to nucleic acid chips, to chromatographic resins, to magnetic particles, to metal particles, to agarose particles, or to other polymer particles. Alternatively, or in addition, the binding agents can be present in the test kits in a form to facilitate their immobilization to surfaces and materials as noted above. The binding agents may be present in a labeled form, for example, labeled with enzymes, fluorescent dyes, fluorescent proteins or protein fragments or peptides, with different isotopes which can be used in mass spectrometry and/or for radioactive measurements, with dyes measurable by chemiluminescence, photometry or by other measurement methods, with organic or inorganic groups such as biotin, chitin, sugars, with lectins, with ligands for receptors or with ligands for other structures.

In a further embodiment, the kit of the present invention may optionally comprise instructions for diagnosing, monitoring the progression or regression, or monitoring the treatment of the renal disorder. The instructions may be on how to use the test kit, how to prepare the samples, what kind of samples to use, how to analyze and interpret the results. The test kit may further comprise instructions on how to use the kit for determining the presence or absence or prognosis of renal failure and of distinct stages of renal failure, especially of chronic and/or acute renal failure.

EXAMPLES

Example 1

Study Design and Probands

Healthy adult humans and humans suspected or known to suffer from renal failure of different stages were enrolled in this study after they provided written informed consent. Laboratory and other parameters, such as body weight, height, age, sex, creatinine in serum and/or urine, and protein in serum and/or urine, were measured. If no 24 h urine sample was available, the creatinine clearance was calculated by use of the Cockcroft formula. Laboratory values determined were leukocytes, nitrite, pH, protein, glucose, ketone, urobilinogen, bilirubin, blood and hemoglobin presence in urine measured using urine sticks. Not all measurements were performed on all subjects. In addition, the past medical history was considered.

The samples were subjected to a standardized protocol including addition of high concentrations of chaotropic salt and ultra filtration, followed by reverse-phase chromatography, followed by MALDI-mass spectrometry of individual fractions of the chromatography, followed by quantitative and qualitative analysis of the resulting data representing fraction, molecular mass and MALDI signal intensity for each detected substance. This procedure led to the identification of mass spectrometric signals suitable to distinguish the different stages of renal failure.

Example 2

Sample Collection and Plasma Preparation

Blood samples were drawn from subjects by venipuncture from a cubital vein, using a 20 gauche needle and a butterfly system with a maximum tubing length of 8 cm. If a tourniquet was applied, it did not remain in place for longer than 1 min. As soon as the blood flowed into the container the tourniquet was released partially. Prior to collecting a blood sample for subsequent plasma preparation, the blood sampling device was flushed with a few ml of the blood not used for plasma preparation. Subsequently, blood was drawn into standard EDTA-containing syringes (e.g., 9 ml EDTA-Monovette, Sarstedt, Nümbrecht, Germany). Within 30 min. of the blood drawing, the blood sample was centrifuged for 10 min. at 2000×g at room temperature. After centrifugation, the plasma was transferred to a fresh tube and subjected to a second centrifugation for 15 min. at 2500×g at room temperature. The resulting, platelet-depleted plasma was transferred to a second fresh tube. Alternatively, aliquots of 1.5 mL plasma from the first centrifugation step were filtered using a 10 mL syringe equipped with a cellulose acetate filter unit with a 0.2 $\mu$M pore size and 5 $cm^2$ filtration area (e.g., Sartorius Minisart®, Sartorius, Gottingen, Germany). All plasma samples in this study were prepared by the 2-step centrifugation method.

Within 30 min. of the preparation, the plasma samples were transferred to a −80° C. freezer and stored until further analyzed.

Example 3

Ultra Filtration of Plasma Samples in the Presence of Chaotropic Salt

After thawing in a water bath, the plasma samples were kept at room temperature until all proteins are re-dissolved. The sample (0.95 mL) was mixed with 3.92 mL of 8 M Guanidin hydrochloride solution, 0.08 mL peptide standard. The pH was adjusted to pH 2-3 by the addition of 0.018 mL of 30% [v/v] HCl. The diluted sample was centrifuged for 60 min. at 4000×g at 23° C. in an ultra filtration device (Amicon Ulta-15, Art. No. UFC 905096, Millipore, Bedford, Mass.). Prior to use, the ultra filtration devices were rinsed with water by adding 15 mL water into the device, centrifugation at 4000×g for 2 min. at 23° C., and discarding any water present in the device after this rinsing step. The final volume of 5.5 mL included 4.3 mL of the resulting filtrate (flow through of the ultrafiltration) diluted with 1.2 mL of 0.1% Tri-Fluor-Acetic Acid (TFA). This sample was stored at −80° C. until further analyzed.

Example 4

Reverse Phase (RP) Chromatography

The separation method carried out was a reverse phase (RP) chromatography. The separation of peptides and proteins was done using a source 5RPC, 4.6×150 mm reverse phase chromatography column (Amersham Biosciences Europe GmbH, Freiburg, Germany). Mobile phases of the following compositions were used: mobile phase A: 0.06% (v/v) tri-fluor-acetic-acid, mobile phase B: 0.05% (v/v) tri-fluor-acetic-acid, 80% (v/v) acetonitrile. The chromatography took place at 33° C. using an HP 1100 with a micro flow cell, both supplied by Agilent Technologies (Boblingen, Germany).

After thawing, samples prepared according to example 3 were centrifuged at 18000·g for 10 minutes. The resulting 0.75 mL plasma equivalent was loaded onto the chromatography column. The chromatography conditions were as follows: 5% mobile phase B at time 0 min, from time 1 to 45 min. continuous increase in the mobile phase B concentration to 50%, from time 45 to 49 min. continuous increase in the mobile phase B concentration to 100%, and subsequently up to time 53 min. constant 100% buffer B. Seven minutes after the start of the chromatography, 96 fractions (0.5 ml each) were collected.

Example 5

Mass Spectrometric Analysis

For mass spectrometric analysis, typical positive ion spectra of peptides were produced in a MALDI-TOF mass spectrometer (matrix-assisted laser desorption ionization). Suitable MALDI-TOF mass spectrometers, such as Voyager-DE, Voyager-DE PRO or Voyager-DE STR, are manufactured by Applied Biosystems (Foster City, Calif.). BIFLEX manufactured by Bruker Daltonik (Bremen, Germany) can also be used.

For the mass spectrometric analysis, the samples were prepared by mixing them with a matrix substance that consists of an organic acid. Suitable matrix substances according to the invention are 3,5-dimethoxy-4-hydroxycinnamic acid, alpha-cyano-4-hydroxycinnamic acid and 2,5-dihydroxy-benzoic acid. A lyophilized equivalent obtained by reverse phase chromatography and corresponding to 0.015 mL plasma was used to measure the peptides and/or proteins and/or standards. The chromatographed sample was dissolved in 0.015 mL of a matrix solution. The matrix solution contains, for example, 10 g/L alpha-cyano-4-hydroxycinnamic acid and 10 g/L L(−) fucose dissolved in a solvent mixture consisting of acetonitrile, water, trifluoroacetic acid and acetone in the ratio 49:49:1:1 by volume. After 0.0003 mL of this solution was transferred to a MALDI carrier plate, the dried sample was analyzed in a Voyager-DE STR MALDI mass spectrometer.

The measurement took place in linear mode with delayed extractionTM. The MALDI-TOF mass spectrometer can be employed to quantify peptides if these peptides are present in a concentration which is within the dynamic measurement range of the mass spectrometer, thus avoiding detector saturation. There is a specific ratio between measured signal and concentration for each peptide, which means that the MALDI mass spectrometry can preferably be used for the relative quantification of peptides. It is possible to measure the signal intensities of the standards and of peptides originating from the sample.

Example 6

Data Analysis

Subsequent to fractionation as described in Example 4, each fraction was individually analyzed by MALDI mass spectrometry as described in Example 5 resulting in 96 mass spectra for each sample. These 96 mass spectra were electronically combined to a so called peptide display. The x-axis of these peptide displays depicts the molecular mass, the y-axis depicts the fraction number and the color intensity represents the mass spectrometric signal intensity.

Data pre-processing involved absolute scaling of MALDI profiles, baseline correction, and m/z-recalibration of the mass spectrometric data. Then spectra were binned down to 1 Da resolution. Subsequent data analyses were performed using 4352 of these signals which had an intensity above 50 units in at least 20% of the samples. The signal intensities were stored using the chromatographic fraction and mass spectrometric m/z ratio as labels. Considering redundancy due to mass/fraction shifts (e.g. the same peptide is present in 2, 3 or more neighboring fractions), oxidation (the same peptide with and without oxidation is present in the sample, without the oxidation being present in the sample at the time the sample was collected) and, double or triple charged peptide forms (the same peptide being detected at multiple positions due to various charge states of it resulting in different mass spectrometric signals of the same molecule), the number of distinct peptides in the analysis was estimated to be about 1500.

Example 7

Mass Spectrometric Sequence Determination

The data of peptide displays were pre-processed by adjusting for background noise. Differences between peptide displays were calculated by subtracting peptide displays from each other electronically. Detection of qualitative or quantitative differences between individual samples or between groups of samples regarding substances present in the samples, such as peptides or proteins, was done by comparison of the mass spectrometric data, e.g. the signal intensities of the corresponding substances. This was done using mass spectrometric signal intensities of individual samples and groups of samples, wherein the groups were samples from healthy versus samples from subjects suffering from different stages of kidney failure.

Peptides were identified using nanoSpray-MS/MS. This entailed a standard peptide ion being selected in the mass spectrometer on the basis of its specific m/z (mass/charge) value in a manner known to the skilled worker. This selected ion was then fragmented by supplying collision energy with an collision gas, e.g. helium or nitrogen, and the resulting fragments of the standard peptide were detected in the mass spectrometer in an integrated analysis unit, and corresponding m/z values were determined (principle of tandem mass spectrometry). The fragmentation behavior of peptides made unambiguous identification of the peptides possible. In this specific case, the mass spectrometric analysis was performed using a Quadrupol-TOF Instrument, QStar-Pulsar model from Applied Biosystems.

While the invention has been illustrated and described in the figures and foregoing description, the same is to be considered as illustrative and not restrictive in character, it being understood that only the preferred embodiments have been shown and described and that all changes and modifications that come within the spirit of the invention are desired to be protected. In addition, all references and patents cited herein are indicative of the level of skill in the art and hereby incorporated by reference in their entirety.

wherein a variance in said quantity of said biomarker in said test sample relative to in said control sample indicates that said subject has or is at risk of developing said renal disorder.

2. A method of identifying a subject having or at risk of developing a renal disorder, comprising:
   a. obtaining a test biological sample from said subject;
   b. determining a quantity of a peptide biomarker in said test sample, wherein said biomarker consists of SEQ ID NO: 2; and
   c. comparing said quantity of said biomarker with a predetermined reference value;
   wherein an increase in said quantity of said biomarker in said test sample relative to said reference value indicates that said subject has or is at risk of developing said renal disorder.

3. A method of monitoring progression of a renal disorder in a subject in need thereof, comprising:
   a. obtaining a test biological sample from said subject;
   b. determining a quantity of a peptide biomarker in said test sample, wherein

---

---

We claim:

1. A method of identifying a subject having or at risk of developing a renal disorder, comprising:
   a. obtaining a test biological sample from said subject;
   b. determining a quantity of a peptide biomarker in said test sample, wherein said biomarker consists of SEQ ID NO: 2;
   c. obtaining a control biological sample from a control subject not having and not at risk of developing said renal disorder;
   d. determining a quantity of said biomarker in said control sample; and
   e. comparing said quantity of said biomarker in said test sample and in said control sample;

i) said biomarker consists of SEQ ID NO: 2, and
   ii) said quantity of said biomarker correlates to a stage of said renal disorder;

c. repeating steps a and b over a period of time; and
   d. comparing said quantities of said biomarker over said period of time;
   wherein a difference in said quantities of said biomarker over said period of time indicates progression of said renal disorder.

4. A method of monitoring efficacy of a renal disorder therapy in a subject in need thereof, comprising:
   a. obtaining a test biological sample from said subject;
   b. determining a quantity of a peptide biomarker in said test sample, wherein i) said biomarker consists of SEQ ID NO: 2, and
ii) said quantity of said biomarker correlates to a stage of said renal disorder;
c. treating said subject with a renal disorder therapy;
d. repeating steps a and b; and
e. comparing said quantity of said biomarker prior to and subsequent to the treatment;
wherein a difference of said quantity of said biomarker prior to and subsequent to the treatment indicates efficacy of said renal disorder therapy.

5. The method of any one of claims 1-4, wherein the subject has a condition selected from the group consisting of injury to a kidney, type 2 diabetes, hypertension, cardiovascular disease, sepsis, hemorrhage, massive blood loss, congestive heart failure, decompensated liver cirrhosis, damaged kidney blood vessels, obstructions of urine collection systems or extra-renal drainage, vasculitis, malignant hypertension, acute glomerulonephritis, acute interstitial nephritis, and acute tubular necrosis.

6. A method of determining an effect of an event on renal function in a subject in need thereof, comprising:
a. obtaining a first test biological sample from said subject prior to said event;
b. obtaining a second test biological sample from said subject subsequent to said event;
c. determining a quantity of a peptide biomarker in said first test sample and in said second test sample, wherein
i) said biomarker consists of SEQ ID NO: 2, and
ii) said quantity of said biomarker correlates to a stage of said renal disorder; and
d. comparing said quantity of said biomarker in said first test sample and in said second test sample;
wherein a difference of said quantity of said biomarker in said first test sample and in said second test sample indicates the effect of said event on renal function.

7. The method of claim 6, wherein said event is selected from the group consisting of exposure to a substance, exposure to a living organism, food ingestion, alcohol ingestion, consumption of tobacco products, exposure to stress, and physical activity.

8. The method of claim 7, wherein said substance is selected from the group consisting of a medication, a chemical, and a toxin.

9. The method of claim 7, wherein said living organism is selected from the group consisting of a plant, an animal, a microbe, and a virus.

10. The method of any one of claims 1-4 and 6, wherein said renal disorder is chronic renal failure, and wherein said stage is selected from the group consisting of Stages 1, 2, 3, 4, and 5 of chronic renal failure.

11. The method of any one of claims 1-4 and 6, wherein said renal disorder is acute renal failure, and wherein said stage is selected from the group consisting of Stages Normal, and R, I, F, L, and E of acute renal failure.

12. The method of claim 4, wherein said renal disorder therapy is a renal replacement therapy selected from the group consisting of medication, hemodialysis and kidney transplantation.

13. The method of any one of claims 1-4 and 6, wherein the step of determining said quantity of said biomarker comprises calculating glomerular filtration rate.

14. The method of claim 13, wherein the step of determining said quantity of said biomarker is accomplished by an immunological method, a molecular biologic method, or a physical method.

15. The method of claim 14, wherein said immunological method is selected from the group consisting of an ELISA assay, an RIA assay, an ELI-Spot assay, a flow cytometry assay, an immunohistochemistry assay, a Western blot analysis, and a protein chip assay.

16. The method of claim 14, wherein said molecular biologic method is selected from the group consisting of a PCR analysis, a RT-PCR analysis, a TaqMan PCR analysis, a nucleic acid chip assay, in situ hybridization, a nucleic acid dot blot analysis, a nucleic acid slot blot analysis, a Southern blot analysis and a Northern blot analysis.

17. The method of claim 14, wherein said physical method is selected from the group consisting of a mass spectrometric method, a FRET assay, a chromatographic assay, and a dye-detection assay.

18. The method of claim 17, wherein said mass spectrometric method is selected from the group consisting of MALDI, ESI, ionspray, thermospray, MCI, FAB, SELDI, ICAT, iTRAQ, and affinity mass spectrometric method.

19. The method of claim 13, wherein the step of determining said quantity of said biomarker is accomplished by nuclear magnetic resonance (NMR), fluorometry, colorimetry, radiometry, luminometry, liquid chromatography, capillary chromatography, thin-layer chromatography, plasmon-resonance (e.g. BIACORE), and one- or two-dimensional gel electrophoresis.

20. The method of any one of claims 1-4 and 6, wherein said biological sample is selected from the group consisting of blood, plasma, serum, hemofiltrate, urine, kidney tissue, in vitro cultured kidney cell lines, in vitro cultured primary kidney cells, in vitro cultured kidney tissue, in vitro cultured kidney organ, and supernatants from in vitro cell culture, tissue culture, or organ culture.

21. The method of claim 20, further comprising fractionating said biological sample prior to the step of determining the quantity of the peptide biomarker in said test sample.

22. The method of claim 21, wherein fractionating said biological sample is accomplished through a method selected from the group consisting of a chromatography method, a filtration method, a capillary electrophoresis method, a gel electrophoresis method, a liquid extraction method, a precipitation method, and an immunoprecipitation method.

23. The method of claim 22, wherein said chromatography method is reverse phase chromatography.

24. The method of any one of claims 1-4 and 6, further comprising calculating glomerular filtration rate by measuring clearance of an endogenic substance.

25. The method of claim 24, wherein said endogenic substance is selected from the group consisting of serum creatinine, Cystatin C, NGAL, urea, interleukin 18, intestinal form of alkaline phosphatease, N-acetyl-beta-gulcosaminidase, alanine-aminopeptidase, kidney injury molecule 1, parathyroid hormone, creatol, creatine kinase, methylguanidine, and 1,5-anhydroglucitol (1,5-AG).

26. The method of any one of claims 1-4 and 6, further comprising a step selected from the group consisting of determining the size of the kidneys, measuring urine output, analyzing urine sediments, and analyzing excretion of sodium or urea.

27. The method of claim 26, wherein the size of the kidneys is determined using an imaging technique.

28. The method of claim 27, wherein said imaging technique is ultrasound.

29. The method of any one of claims 1-4 and 6, wherein said subject is selected from the group consisting of a human, a primate, a mouse, a dog, a pig, and a rat.

30. The method of any one of claims 1-4 and 6, wherein determining the quantity of a peptide biomarker comprises contacting the test sample with an antibody or antigen binding fragment thereof that specifically binds to the peptide biomarker consists of SEQ ID NO: 2.

\* \* \* \* \*